United States Patent
Donovan

(10) Patent No.: US 7,982,003 B2
(45) Date of Patent: Jul. 19, 2011

(54) CREATING DESIGNER ANTIMICROBIALS; PEPTIDOGLYCAN HYDROLASE MODULE SHUFFLING

(75) Inventor: David M. Donovan, Baltimore, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/498,171

(22) Filed: Jul. 6, 2009

(65) Prior Publication Data

US 2010/0028324 A1 Feb. 4, 2010

Related U.S. Application Data

(62) Division of application No. 11/294,156, filed on Dec. 5, 2005, now Pat. No. 7,572,602.

(60) Provisional application No. 60/633,280, filed on Dec. 3, 2004.

(51) Int. Cl.
*C07K 1/00* (2006.01)
*C12N 9/00* (2006.01)
*C12N 9/14* (2006.01)
*C12N 9/48* (2006.01)
*C12N 9/52* (2006.01)
*A61K 38/43* (2006.01)

(52) U.S. Cl. ........ 530/350; 435/183; 435/195; 435/212; 435/220; 424/94.1

(58) Field of Classification Search ........................ None
See application file for complete search history.

(56) References Cited

U.S. PATENT DOCUMENTS
2010/0158886 A1 * 6/2010 Donovan et al. ............. 424/94.3

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp: 8-9, 2002.*
MESH search results for "peptidoglycan hydrolase". Retrieved from the Internet <URL:http://www.ncbi.nlm.nih.gov/sites/entrez?db=mesh>.*
MESH search results for "endolysin". Retrieved from the Internet <URL:http://www.ncbi.nlm.nih.gov/sites/entrez?db=mesh>.*

* cited by examiner

*Primary Examiner* — Suzanne M Noakes
*Assistant Examiner* — Jae W Lee
(74) *Attorney, Agent, or Firm* — John D. Fado; Evelyn M. Rabin

(57) ABSTRACT

The invention concerns a nucleic acid encoding a recombinant bifunctional fusion peptidoglycan hydrolase protein formed from a nucleic acid encoding a peptidoglycan hydrolase module and a nucleic acid encoding a second peptidoglycan hydrolase module. The fusion, dual (or multiples thereof) peptidoglycan hydrolase modules can be used to treat disease caused by the bacteria for which the individual modules of the fusion protein are specific.

6 Claims, 4 Drawing Sheets

SEQUENCE LISTING

```
<160> NUMBER OF SEQ ID NOS: 9

<210> SEQ ID NO 1
<211> LENGTH: 1880
<212> TYPE: DNA
<213> ORGANISM: Streptococcus phage B30

<400> SEQUENCE: 1
ccacgagcca aaaaaatagg aggggacatg cgagcaatca ctaaaatagc aatggtacta      60
gcgatagcaa tcctgtacat accgcttgca gtgattgctt tttttattta tccgatttat    120 ttccttttg gaaaggagga gtaaatggca acttatcaag aatataaaag caggtcaaat     180
ggtaacgctt atgatattga tgggtctttc ggtgcacaat gttgggatgg ctacgcagat    240
tactgtaagt atctaggact gccatacgca aactgtacaa atacaggata cgcaagggat    300
atatgggagc aacgtcacga aaatggtatc ttaaactatt ttgatgaagt ggaagttatg    360
caagctggtg atgttgctat ttttatggtt gttgacggtg taacgcctta cagtcatgta    420 gcaattttg acagcgatgc aggaggcgga tatggctggt ttttggggca aaatcaaggg     480
ggtgctaacg gtgcatacaa tcttgtaaaa atcccatatt cagcaactta tccaacagcc    540
tttagaccaa aaagctttaa aaacgctgtt actgtaactg ataataccgg tttaaataaa    600
ggtgattact ttatcgatgt atcggcttat caacaagcag atttaacaac gacttgtcag    660
caggcgggca ctacaaaaac gattatcaag gtatccgagt caattgcttg gctgtctgac    720
agacatcaac aacaagcaaa cacaagcgac ccaattggct attaccactt tggacgtttt    780
ggcggtgata gtgctttagc gcaacgggaa gcagacttat ttttgtctaa cttaccaagc    840
aaaaaagtat catacttagt cattgactat gaagattccg caagcgcaga caagcaagct    900
aacacaaatg cagttattgc atttatggat aaaatcgcta gcgctggata taagcctatt    960
tattacagct ataaaccatt tacgcttaat aatattgatt atcagaaaat tatcgctaag   1020
taccctaata gcatttggat agctggttat ccagactacg aagtacgaac agagccgctg   1080
tgggagttct tccccttcaat ggatggtgtt cgctggtggc agtttacaag tgtaggagta   1140
gcaggtggtt tagataaaaa tattgtgttg ttagcagatg atagtagcaa aatggatata   1200
cctaaggttg ataagccaca agaacttact ttttatcaaa aactagctac taacactaaa   1260
ttagacaact caaatgtacc ttattacgaa gcaactctta gcacagacta ttatgtagag   1320
tctaagccaa acgcaagtag cgctgataaa gaatttatca aggcaggaac tcgtgtaaga   1380
gtttatgaaa aagtgaatgg atggtcacgc attaaccatc cagagtcggc gcaatgggta   1440
gaagataact acttagttaa cgcaacagat atgtaaaaat aaacgaaagg aaaagctcct   1500
ttagataaga caaatgccct cgctttgcgg gggctatttt tattgaaata ttgaaatctc   1560
tttataaaaa tagtaaaata gtttcgctat tataaagaaa gttgttatca atgaataatc   1620
tagttcttcc tcagaattta aacaaatata acattacgaa aatcgttacc aatttcaata   1680
gattacttgc tttaagtgat aacaggacac ttacagtaga tatgagaaac attgagtttg   1740
cggaacctag tggagtaatt tcgttatata atatgttaac ttttgctaca aaagaaaag   1800
```

```
atgcaaacat caagtggtta atatgcgaag aaagctcttt aaataaacgt caaaggcaag    1860
ctatgttgta tctagtagat                                                1880
```

<210> SEQ ID NO 2
<211> LENGTH: 443
<212> TYPE: PRT
<213> ORGANISM: Streptococcus phage B30

<400> SEQUENCE: 2

```
Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Leu Val Lys Ile Pro Tyr Ser Ala Thr
        115                 120                 125

Tyr Pro Thr Ala Phe Arg Pro Lys Ser Phe Lys Asn Ala Val Thr Val
    130                 135                 140

Thr Asp Asn Thr Gly Leu Asn Lys Gly Asp Tyr Phe Ile Asp Val Ser
145                 150                 155                 160

Ala Tyr Gln Gln Ala Asp Leu Thr Thr Thr Cys Gln Gln Ala Gly Thr
                165                 170                 175

Thr Lys Thr Ile Ile Lys Val Ser Glu Ser Ile Ala Trp Leu Ser Asp
            180                 185                 190

Arg His Gln Gln Gln Ala Asn Thr Ser Asp Pro Ile Gly Tyr Tyr His
        195                 200                 205

Phe Gly Arg Phe Gly Gly Asp Ser Ala Leu Ala Gln Arg Glu Ala Asp
    210                 215                 220

Leu Phe Leu Ser Asn Leu Pro Ser Lys Lys Val Ser Tyr Leu Val Ile
225                 230                 235                 240

Asp Tyr Glu Asp Ser Ala Ser Ala Asp Lys Gln Ala Asn Thr Asn Ala
                245                 250                 255

Val Ile Ala Phe Met Asp Lys Ile Ala Ser Ala Gly Tyr Lys Pro Ile
            260                 265                 270

Tyr Tyr Ser Tyr Lys Pro Phe Thr Leu Asn Asn Ile Asp Tyr Gln Lys
        275                 280                 285

Ile Ile Ala Lys Tyr Pro Asn Ser Ile Trp Ile Ala Gly Tyr Pro Asp
    290                 295                 300

Tyr Glu Val Arg Thr Glu Pro Leu Trp Glu Phe Phe Pro Ser Met Asp
305                 310                 315                 320

Gly Val Arg Trp Trp Gln Phe Thr Ser Val Gly Val Ala Gly Gly Leu
                325                 330                 335

Asp Lys Asn Ile Val Leu Leu Ala Asp Asp Ser Ser Lys Met Asp Ile
            340                 345                 350

Pro Lys Val Asp Lys Pro Gln Glu Leu Thr Phe Tyr Gln Lys Leu Ala
        355                 360                 365
```

```
Thr Asn Thr Lys Leu Asp Asn Ser Asn Val Pro Tyr Tyr Glu Ala Thr
        370                 375                 380

Leu Ser Thr Asp Tyr Tyr Val Glu Ser Lys Pro Asn Ala Ser Ser Ala
385                 390                 395                 400

Asp Lys Glu Phe Ile Lys Ala Gly Thr Arg Val Arg Val Tyr Glu Lys
                405                 410                 415

Val Asn Gly Trp Ser Arg Ile Asn His Pro Glu Ser Ala Gln Trp Val
        420                 425                 430

Glu Asp Asn Tyr Leu Val Asn Ala Thr Asp Met
        435                 440

<210> SEQ ID NO 3
<211> LENGTH: 768
<212> TYPE: DNA
<213> ORGANISM: Staphylococcus simulans

<400> SEQUENCE: 3
catatggcaa cacatgaaca ttcagcacaa tggttgaata attacaaaaa aggatatggt      60
tacggccctt atccattagg tataaatggc ggtatgcact acggagttga ttttttatg     120 aatattggaa caccagtaaa agctatttca agcggaaaaa tagttgaagc tggttggagt     180
aattacggag aggtaatca ataggtctt attgaaaatg atggagtgca tagacaatgg     240
tatatgcatc taagtaaata taatgttaaa gtaggagatt atgtcaaagc tggtcaaata     300
atcggttggt ctggaagcac tggttattct acagcaccac atttacactt ccaaagaatg     360
gttaactcat tttcacagtc aactgcccaa gatccaatgc ctttcttaaa gagcgcagga     420
tatggaaaag caggtggtac agtaactcca acgccgaata caggttggaa aacaaacaaa     480
tatggcacac tatataaatc agagtcagct agcttcacac ctaatacaga tataataaca     540
agaacgactg gtccatttag aagcatgccg cagtcaggag tcttaaaagc aggtcaaaca     600
attcattatg atgaagtgat gaaacaagac ggtcatgttt gggtaggtta tacaggtaac     660
agtggccaac gtatttactt gcctgtaaga acatggcaga agtctactaa tactctgggt     720
gttctgtggg gaactataaa gctcgagcac caccaccacc accactga                 768

<210> SEQ ID NO 4
<211> LENGTH: 255
<212> TYPE: PRT
<213> ORGANISM: Staphylococcus simulans

<400> SEQUENCE: 4

His Met Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Gln Ser Thr
```

```
                115                 120                 125
Ala Gln Asp Pro Met Pro Phe Leu Lys Ser Ala Gly Tyr Gly Lys Ala
        130                 135                 140

Gly Gly Thr Val Thr Pro Thr Pro Asn Thr Gly Trp Lys Thr Asn Lys
145                 150                 155                 160

Tyr Gly Thr Leu Tyr Lys Ser Glu Ser Ala Ser Phe Thr Pro Asn Thr
                165                 170                 175

Asp Ile Ile Thr Arg Thr Thr Gly Pro Phe Arg Ser Met Pro Gln Ser
            180                 185                 190

Gly Val Leu Lys Ala Gly Gln Thr Ile His Tyr Asp Glu Val Met Lys
        195                 200                 205

Gln Asp Gly His Val Trp Val Gly Tyr Thr Gly Asn Ser Gly Gln Arg
    210                 215                 220

Ile Tyr Leu Pro Val Arg Thr Trp Gln Lys Ser Thr Asn Thr Leu Gly
225                 230                 235                 240

Val Leu Trp Gly Thr Ile Lys Leu Glu His His His His His
                245                 250                 255

<210> SEQ ID NO 5
<211> LENGTH: 21
<212> TYPE: DNA
<213> ORGANISM: Unknown
<220> FEATURE:
<223> OTHER INFORMATION: Chemically Synthesized

<400> SEQUENCE: 5
tccggcgtag aggatcgaga t                                              21

<210> SEQ ID NO 6
<211> LENGTH: 21
<212> TYPE: DNA
<213> ORGANISM: Unknown
<220> FEATURE:
<223> OTHER INFORMATION: Chemically Synthesized

<400> SEQUENCE: 6
tgctacatgc tcgagaggcg t                                              21

<210> SEQ ID NO 7
<211> LENGTH: 30
<212> TYPE: DNA
<213> ORGANISM: Unknown
<220> FEATURE:
<223> OTHER INFORMATION: Chemically Synthesized

<400> SEQUENCE: 7
gccctcagtc gacactagtc cacagaacac                                     30

<210> SEQ ID NO 8
<211> LENGTH: 36
<212> TYPE: DNA
<213> ORGANISM: Unknown
<220> FEATURE:
<223> OTHER INFORMATION: Chemically Synthesized

<400> SEQUENCE: 8
ttcgatatcg cggccgcaac catggcaact tatcaa                              36

<210> SEQ ID NO 9
<211> LENGTH: 28
<212> TYPE: DNA
<213> ORGANISM: Unknown
<220> FEATURE:
```

<223> OTHER INFORMATION: Chemically Synthesized

<400> SEQUENCE: 9
ctttcggaat tcgttagcag ccggaatc                      28

CREATING DESIGNER ANTIMICROBIALS; PEPTIDOGLYCAN HYDROLASE MODULE SHUFFLING

REFERENCE TO RELATED APPLICATION

This application is a divisional application of application Ser. No. 11/294,156, filed Dec. 5, 2005, now U.S. Pat. No. 7,572,602, which claims the benefit of U.S. Provisional Application No. 60/633,280, filed Dec. 3, 2004, which is incorporated herein by reference in its entirety.

BACKGROUND OF THE INVENTION

1. Field of the Invention

This invention relates to a nucleic acid encoding a multifunctional antimicrobial fusion protein formed from a nucleic acid encoding a functional module or domain of a particular peptidoglycan hydrolase, e.g., an endolysin which specifically attacks the peptidoglycan cell wall of a bacteria of one genus, specie or substrain in combination with additional nucleic acids encoding functional modules or domains of other peptidoglycan hydrolases which specifically attack the peptidoglycan cell walls of additional bacteria from different genus, specie or substrains. A preferred embodiment relates to an isolated bifunctional peptidoglycan hydrolase fusion protein, wherein one module of the fusion endolysin is specific for a specific bond in the peptidoglycan wall of *Staphylococcus aureus* and the second module is specific for a specific bond in the peptidoglycan wall of *Streptococcus* spp. (*agalactiae, dysgalactia* and, *uberis*). The invention further relates to methods of treating diseases caused by the bacteria for which the individual modules of the fusion protein are specific.

2. Description of the Relevant Art

Novel antimicrobials are desperately needed to stem the tide of increasing incidence of antimicrobial resistance. The social and economic impact of such resistance has been summarized and characterized as "accumulating and accelerating, while the world's tools for combating it decrease in power and number: More than 90 percent of *Staphylococcus aureus* strains are resistant to penicillin and other related antibiotics. There is an alarming rise in the incidence of enterococci (the *streptococcus* that is the most common cause of hospital-acquired infections) resistant to the antibiotic vancomycin, often the last weapon for defeating these pathogens. As many as 40 percent of strains of pneumococci in some parts of the United States are now partly or completely resistant to penicillin and a number of antibiotics. The cost of these dynamics, especially multidrug resistance, is also rising—in terms of mortality, disability, and dollars. Antibiotic-resistant bacteria generate a minimum of $4 billion to $5 billion in costs to U.S. society and individuals yearly, and in 1992, the 19,000 deaths directly caused by hospital-acquired infections made them the eleventh leading cause of death in the U.S. population." (1998. Workshop Summary of the Forum on Emerging Infections, In: *Antimicrobial Resistance: Issues and Options*, Harrison and Lederberg, eds., Institute of Medicine, National Academy Press, Washington, D.C., page 1.)

Antibiotic-resistant bacteria are also of concern with regard to animal diseases. In the USA alone, losses due to mastitis are estimated to be between $1.7 billion (Bramley et al. 1996. In: Current Concepts of Bovine Mastitis, 4[th] Edition, National Mastitis Council, Inc., Madison, Wis.) and $2 billion annually (Sordillo of al. 2002. *J. Mammary Gland Biol. Neoplasia* 7(2): 135-146). In a recent regional survey of mastitis in the Pennsylvania and New York, *Staphylococcus aureus* and *Streptococcus agalactiae* (Group B *Streptococcus*; GBS) were each shown to be responsible for up to 20% of the mastitis in this region (Wilson et al. 1997. *J. Dairy Sci.* 80(10): 2592-2598). *Streptococcus dysgalactiae* (Group C *Streptococcus*; GCS) and *Streptococcus uberis* are also serious mastitis-causing pathogens in the USA, with *S. uberis* also being responsible for 20% of the mastitis in the UK (Veterinary Laboratories Agency & Scottish Agricultural College Survey).

These bacteria are causative agents for both animal and human diseases. *S. aureus*, GBS and GCS, are also known human pathogens with 90% of the isolated *S. aureus* strains showing drug resistance (see above). GBS is a major neonatal pathogen. Up to 20% of pregnant women are colonized vaginally with GBS that can result in potentially fatal neonatal infections (Regan et al. 1996. *Am. J. Obstet. Gynecol.* 174(4): 1354-1360). GCS has recently been shown to be a cause of acute pharyngitis in children (Zaoutis et al. 2004. *Clin. Microbiol. Infect.* 10(1): 37-40).

A recurring theme in the quest for new antimicrobials is the use of bacteriophage therapy. Bacteriophage are viruses that attack bacteria. Bacteriophage therapy has been in existence for nearly 100 years having reached its popularity in Eastern Europe in the early 1900s, but fell out of favor after the discovery of antibiotics in the mid 1900s (reviewed by Mathur et al. 2003. *J. Assoc. Physicians India* 51: 593-596). The phage infects a single cell, replicates itself within the host cell, and then explodes the host cell releasing the progeny phage which then go on to repeat the cycle. Each phage genome codes for lytic proteins that degrade the bacterial cell wall peptidoglycan and allow the phage to escape.

Peptidoglycans are a major structural component of both Gram positive and Gram negative bacterial cell walls. They are the major strength element of the bacterial cell wall, are up to 40 layers thick, and are composed of a complex molecule with a sugar backbone (alternating N-acetyl glucosamine and N-acetyl muramic acid residues). This backbone is cross linked with covalently attached peptides, allowing the bacteria to withstand the 3-4 atmospheres of osmotic pressure that exists across the bacterial cell wall, see FIG. 1 (Chatterjee et al. 1977. *J. Theor. Biol.* 68(3): 385-390). Although peptidoglycan structure is similar between species, with the oligosaccharide backbone present in all, there is also a great deal of cell wall diversity between different bacterial species.

Bacteriophage are very specific and usually limited in their host range, thus a single strain of phage will not infect or kill all bacteria. This specificity is in part derived from the specificity of their lytic genes (namely endolysins) for a specific covalent bond in the cell wall peptidoglycan. At this time, there are four major classes of enzymatic activities which have been identified in endolysins that can degrade peptidoglycan, 1) N-acetyl muramidase (lysozyme like), 2) N-acetylglucosaminidase, 3) N-acetylmuramyl-L-alanine amidase and 4) endopeptidase (FIG. 1).

Endolysins are modular in nature with each module harboring a specific enzymatic activity. These modular sequences are highly conserved between phages that have very different host ranges. It is also common to have multiple modules linked together to form a single endolysin, that can then attack the cell wall peptidoglycan at multiple sites in the molecule. A well characterized example is the *Streptococcus pneumoniae* phage Dp-1 endolysin which has a choline binding domain at the carboxyl terminus and an amidase module at the amino terminus (Garcia et al. 1988. *Proc. Natl. Acad. Sci. U.S.A.* 85: 914-918). Choline binding is necessary for full enzymatic activity. The choline-binding module may have been obtained through horizontal transfer from a *Lactobacil*-

*lus* strain, while the amidase domain was likely obtained from a *Streptococcus* autolysin, lytA. The choline domain can be exchanged between various gram positive bacteria and their bacteriophage enzymes and still maintains its function (Lopez et al. 1997. *Microb. Drug Resist.* 3(2): 199-211).

These mastitis-causing strains are killed by endolysins: *Streptococcus agalactiae, S. dysgalactiae* (Pritchard et al. 2004. *Microbiology* 150(7): 2079-2087) and *S. uberis* (personal communication, David Donovan), are killed by B30 endolysin; *Staphylococcus aureus* and some coagulase negative *Staphylococcus*, are killed by lysostaphin (Cisani et al. 1982. *Antimicrob. Agents and Chemo.* 21:531-535).

In the quest for antimicrobials against mastitis-causing bacteria, agents must be found that can target our pest organisms very specifically. This is not just to reduce the potential for resistance development, but also to prevent damage to commercially important organisms that are necessary for the downstream processing of milk into yogurt and cheese. The prevention of mastitis would not just benefit animal health, but also food quality. Any antimicrobial that is specific for a given pathogen will potentially reduce the use of broad range antibiotics and thus help prevent the onslaught of multi drug resistant varieties.

Thus, to counter the rise of drug resistant pathogenic bacteria, there is a need for new specific antimicrobial treatments. Reagents shown to be very specific for the genera, species or substrains of concern would give better effective control of economically important diseases and would therefore be ideal candidates for therapeutic treatments.

SUMMARY OF THE INVENTION

We have discovered that the fusion of the nucleic acid encoding two endolysins, lysostaphin and an endolysin from the Group B *Streptococcus* B30 bacteriophage, generates a chimeric nucleic acid encoding a bifunctional endolysin fusion protein which is specific for the peptidoglycan cell wall of two genera of gram positive bacteria, *Streptococcus* and *Staphylococcus*, and which is capable of lysing multiple species between the two genera.

In accordance with this discovery, it is an object of the invention to provide a novel chimeric nucleic acid reagent for obtaining a novel antimicrobial bifunctional fusion protein reagent capable of specifically lysing more than one genus, specie or substrain of pathogenic bacteria.

It is an object of the invention to provide a nucleic acid encoding an antimicrobial fusion protein formed from a nucleic acid encoding a functional module or domain of a particular bacteriophage endolysin which specifically attacks the peptidoglycan cell wall of bacteria of one bacterial genus, for example, *Streptococcus*, in combination with nucleic acid encoding functional module or domain of a second endolysin, a bacterial endolysin, which specifically attacks the peptidoglycan cell wall of bacteria of a second bacterial genus, for example, *Staphylococcus*.

It is also an object of the invention to provide an antimicrobial fusion or chimeric protein, a fusion endolysin, which is functional, i.e., retains its properties for attacking the peptidoglycan cell wall of gram positive bacteria and comprises a functional module or domain of a particular bacteriophage endolysin which specifically attacks the peptidoglycan cell wall of a pathogenic bacteria of one genus, e.g., *Streptococcus*, in combination with a functional module or domain of a second endolysin, a bacterial endolysin, which specifically attacks the peptidoglycan cell wall of a pathogenic bacteria of a second genus e.g., *Staphylococcus*.

Another object of the invention relates to a strategy of generating a nucleic acid sequence encoding a chimeric endolysin according to the invention.

An added object of the invention is to provide a nucleic acid sequence encoding a chimeric endolysin according to the invention as an encoding sequence which allows disease resistance to be imparted to the organism. It is well understood that this sequence can also be used in combination with another sequence, or sequences, encoding one or more disease resistant properties.

A further object of the invention also relates to a chimeric gene (or expression cassette) comprising an encoding sequence as well as heterologous regulatory elements in positions 5' and 3' which can function in a host organism, the encoding sequence comprising at least one nucleic acid sequence encoding a fusion endolysin.

An additional object of the invention is to provide a host organism into which the chimeric gene according to the invention can be introduced so as to produce a fusion endolysin.

An added object of the invention is to provide compositions useful for the treatment of disease caused by the bacteria for which the individual modules of the fusion protein are specific.

Also part of this invention is a kit, comprising a composition for treatment of disease caused by the bacteria for which the individual modules of the fusion protein are specific.

Other objects and advantages of this invention will become readily apparent from the ensuing description.

BRIEF DESCRIPTION OF THE DRAWINGS

FIG. 4A depicts the analysis of the endolysin B30-443 and the fusion protein 443-Lyso. Lane M, Markers; Lanes 1 and 2, SDS-PAGE of *E. coli* crude extract and purified B30-443, respectively; Lane 3 SDS-PAGE of *E. coli* crude extract of 443-Lyso; Lanes 4 and 5, zymogram with *S. agalactiae* of *E. coli* crude extract and purified B30-443, respectively; Lane 6, zymogram with *S. agalactiae* and *E. coli* crude extract of 443-Lyso; Lane 7, zymogram with *S. aureus* and *E. coli* crude extract of 443-Lyso. The fusion 443-Lyso was not constructed with a His tag and thus was not purified. FIG. 4B shows the analysis of the truncated endolysin B30-182 and the fusion protein 182-Lyso. Lane M, Markers; Lanes 1 and 2, SDS-PAGE of *E. coli* crude extract and purified B30-182, respectively; Lanes 3 and 4, SDS-PAGE of *E. coli* crude extract and purified 182-Lyso, respectively; Lanes 5 and 6 zymogram with *S. agalactiae* of *E. coli* crude extract and purified B30-182, respectively; Lanes 7 and 8, zymogram with *S. agalactiae* of *E. coli* crude extract and purified 182-Lyso, respectively; Lanes 9 and 10, Zymogram with *S. aureus* of *E. coli* crude extract and purified 182-Lyso, respectively.

DETAILED DESCRIPTION OF THE INVENTION

Figure 1:
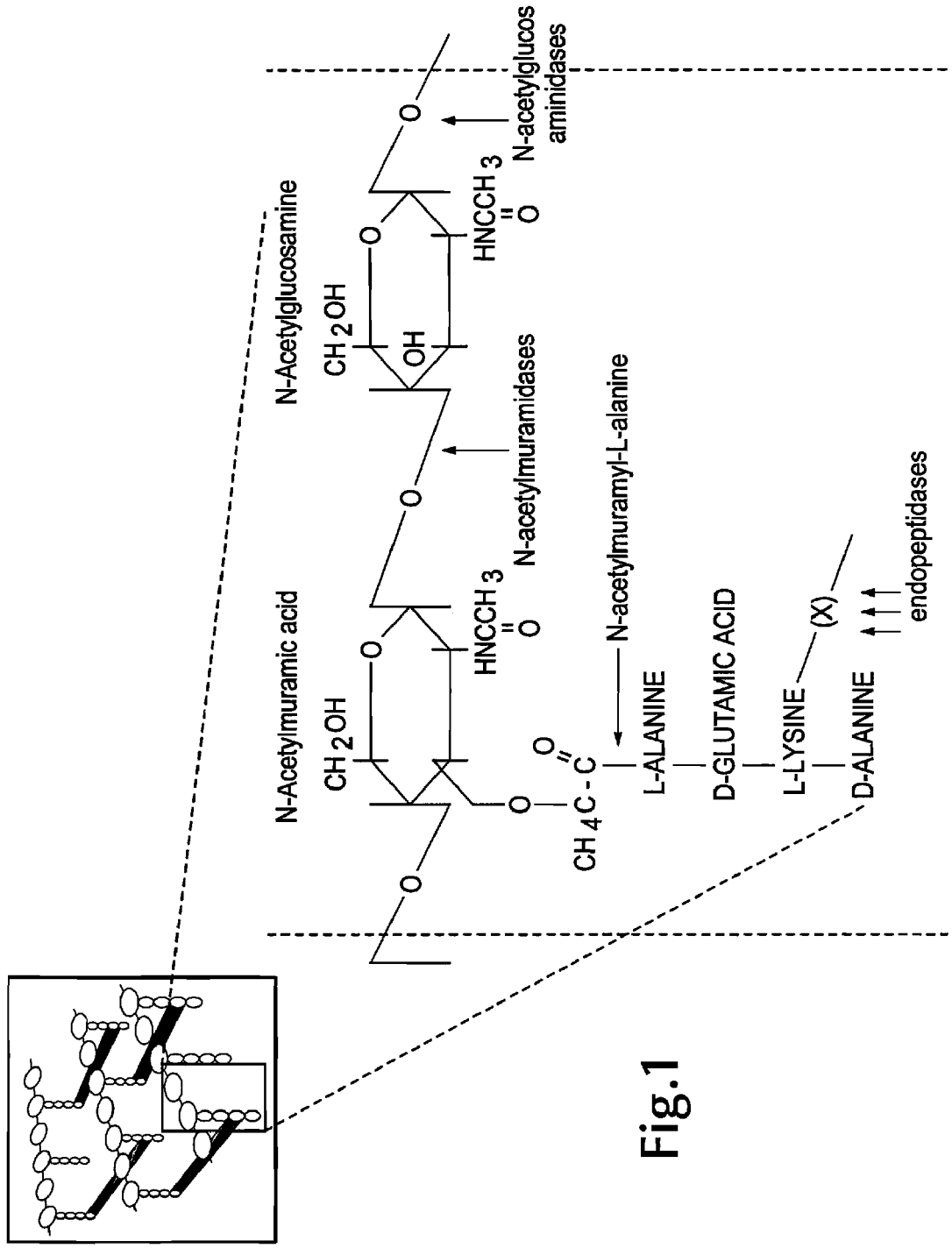
FIG. 1 depicts a typical peptidoglycan structure showing the glycan chain, peptide linkages, and crosslinking sites. (X) refers to amino acids which may crosslink one tetrapeptide to another. The arrows represent sites of cleavage by bacteriolytic enzymes: (1) N-acetylmuramidases, (2) N-acetylglucosaminidases, (3) N-acetyl-muramyl-L-alanine amidases, and (4) endopeptidases.

The increased incidence of bacterial antibiotic resistance has led to a renewed search for novel antimicrobials. The invention relates to the design and creation of new antimicrobials by generating recombinant multifunctional fusion endolysin proteins by the fusion of nucleic acid sequences encoding bacteriophage or bacterial endolysin modules which are specific for the peptidoglycan cell wall of phylogenetically different bacteria, i.e., bacteria belonging to different genera, species or substrains. Each portion of the fusion endolysin is derived from an endolysin of any origin and is, in particular, selected from amongst Gram positive and Gram negative bacteria and their bacteriophage. Furthermore, activity modules from other types of molecules e.g., lysozyme, and from other types of organisms, e.g., trout, can also additionally be used to generate antimicrobials of interest.

According to the preferred embodiment of the invention, the functional module or domain of a particular bacterial endolysin (lysostaphin) which specifically attacks the peptidoglycan cell wall of *Staphylococcus aureus* is derived from *Staphylococcus simulans*.

According to another preferred embodiment of the invention, the functional module or domain of a second endolysin which specifically attacks the peptidoglycan cell wall of *Streptococcus agalactiae* is derived from GBS bacteriophage B30. A number of endolysins and their primary sequences have been described in the prior art, especially phage and prophage endolysins from both Gram positive and Gram negative bacteria such as *Pseudomonas, Escherichia coli, Enterococcus, Bacillus, Clostridium, Pneumococcus* (for reviews see Rigden et al. 2003. *Trends in Biochem. Sci.* 28: 230-234).

*Staphylococcus aureus* and *Streptococcus agalactiae* are mastitis-causing organisms as well as human pathogens. The antimicrobial protein of the invention has been designed to specifically attack both pathogens. Thus, in treating mastitis, both pathogens could be treated with a single bifunctional fusion endolysin protein and the cell walls of both can thus be targeted. Two peptidoglycan hydrolase domains, each targeting a different genus of bacteria, were fused to create a novel antimicrobial protein that is effective against both pathogen's.

Furthermore, in addition to these bifunctional fusion peptidoglycan hydrolase proteins, using the strategy of the invention, recombinant multifunctional fusion antimicrobial proteins can be generated. Nucleic acid sequences encoding more than two functional peptidoglycan hydrolase modules and/or encoding peptidoglycan hydrolase modules which are specific for the peptidoglycan cell wall of more than two types of bacteria, i.e., bacteria belonging to more than two different genera, species or substrains can be generated.

Bacteriophage endolysins, as described above, are bacteriophage-encoded enzymes which degrade the peptidoglycan component of the bacterial cell wall to allow the bacteriophage to escape. Endolysins usually attack the peptidoglycan from inside the cell wall, where they are released during cell lysis by the bacteriophage. However, it was shown that exposure of susceptible bacteria to preparations of the endolysin are often sufficient to lyse Gram positive bacteria from the outside in both in vitro and in vivo settings (Nelson et al. 2001. *Proc. Natl. Acad. Sci. U.S.A.* 98 (7): 4107-4112; Schuch et al. 2002. *Nature* 418(6900): 884-889; Loeffler et al. 2001. *Science* 294(5549): 21270-21272). The peptidoglycan lytic activities of peptidoglycan hydrolases (endolysins) (N-acetylmuramidases, N-acetylglucosaminidases, N-acetylmuramyl-L-alanine amidases, and endopeptidases) have been localized to short modular domains (~100-200 amino acids), any one of which is sufficient to lyse the host cell. Endolysin substrate binding domains have been characterized via intrageneric fusions of endolysin modules (Lopez et al., supra).

Lysostaphin is encoded by the bacterial genome of *Staphyloccus simulans*. It was discovered in 1964 as a secreted protein of *S. simulans* which was shown to kill *Staphyloccus aureus* (Schindler and Schuhart. 1964. *Proc. Natl. Acad. Sci. U.S.A.* 51: 414-421) and more recently, multi drug resistant varieties (Bhakta et al. 2003. *Indian J. Med. Res.* 117: 146-151). This endopeptidase has an activity that is specific for the *S. aureus* peptidoglycan pentaglycine bridge and is effective against other Staphylococci as well, including mastitis-causing coagulase-negative staph (CNS) (Cisani et al. 1982. *Antimicrob. Agents Chemother.* 21(4): 531-535). Lysostaphin has no reported activity against any Streptococci.

Figure 2:
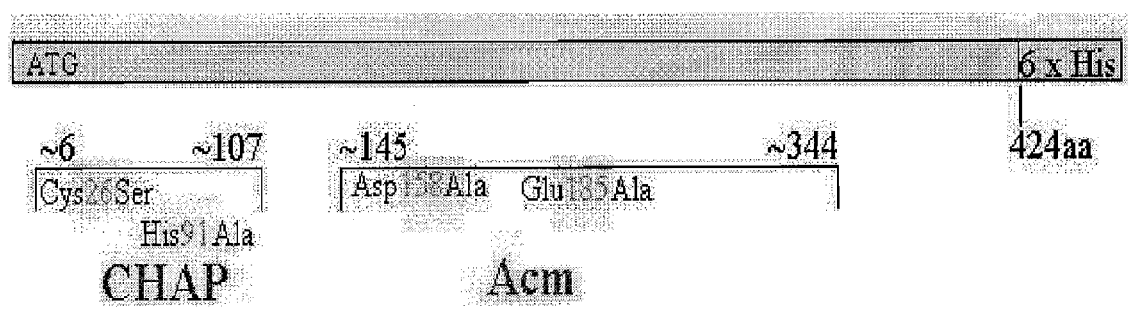
FIG. 2 depicts a schematic of B30 endolysin and conserved CHAP endopeptidase and Acm glycolase domains. Highly conserved amino acids were subjected to site-directed mutagenesis (Pritchard et al., supra) and demonstrated to be essential for domain function.

The B30 endolysin recognizes and degrades *Streptococcus* cell wall peptidoglycan. The *S. agalactiae* bacteriophage B30 endolysin gene (SEQ ID NO:1) was recently cloned and characterized (Pritchard et al., supra). It is not a secreted protein, but a cytoplasmic phage endolysin that is synthesized and released when B30 infects a suitable host. The B30 endolysin harbors two modules, a D-alanyl-L-alanine endopeptidase amino terminus (CHAP) domain and an Acm glycolase (lysozyme-like) domain near the carboxyl terminus. The B30 endolysin has no reported activity against *S. aureus*. Two essential amino acids in each of these B30 endolysin domains have been defined by site-directed mutagenesis and are illustrated in FIG. 2 (Pritchard et al., supra).

The present invention equally relates to a nucleic acid sequence encoding an above-described chimeric endolysin. According to the present invention, "nucleic acid sequence" is to be understood as being a nucleotide sequence which can be of the DNA or the RNA type preferably of the DNA type, especially double-stranded whether it is natural or synthetic origin. This will also include a DNA sequence for which the codons encoding the chimeric endolysin according to the invention will have been optimized according to the host organism in which it will be expressed, these optimization methods being well known to those skilled in the art.

The term "transgene" is understood to describe genetic material which has been or is about to be artificially inserted into the genome of a non-human animal, and particularly into a cell of a living non-human mammal.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance.

The term "construct" refers to a recombinant nucleic acid, generally recombinant DNA, that has been generated for the purpose of the expression of a specific nucleotide sequence(s), or is to be used in the construction of other recombinant nucleotide sequences.

The term "operably linked" refers to a functional connection between a DNA sequence and a regulatory sequence(s), e.g., a DNA sequence and a regulatory sequence(s) are connected in such a way as to permit gene expression when the appropriate molecules (e.g., transcriptional activator proteins) are bound to the regulatory sequence(s).

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequences encoding each module of the chimeric endolysin are of bacterial (lysostaphin), eukaryotic (trout) or bacteriophage origin.

The encoding sequences of the individual modules of the fusion endolysin according to the invention can be assembled by any usual method for constructing and assembling nucleic acid fragments which are well known to those skilled in the art and widely described in the literature and illustrated especially by the use examples of the invention.

The present invention therefore also relates to a strategy of generating a nucleic acid sequence encoding a chimeric endolysin according to the invention, this process being defined herein above and in the examples.

Another subject of the invention is the use of a nucleic acid sequence encoding a chimeric peptidoglycan hydrolase according to the invention as an encoding sequence which allows disease resistance to be imparted to the organism. It is well understood that this sequence can also be used in combination with another sequence, or sequences, encoding one or more disease resistant properties.

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding a chimeric peptidoglycan hydrolase as defined above.

By host organism there is to be understood any single-celled or lower or higher multi-celled organism into which the chimeric gene according to the invention can be introduced so as to produce chimeric peptidoglycan hydrolase.

The regulatory elements required for expressing the nucleic acid sequence encoding a peptidoglycan hydrolase are well known to those skilled in the art and depend on the host organism. They comprise, in particular, promoter sequences, transcription activators, terminator sequences, inclusive of start and stop codons. The means and methods for identifying and choosing the regulatory elements are well known to those skilled in the art and widely described in the literature.

The present invention also relates to the fusion protein, the chimeric peptidoglycan hydrolase protein, the two elements of the fusion protein being defined further above.

The present invention also relates to a cloning and/or expression vector for transforming a host organism containing at least one chimeric gene as defined hereinabove. This vector comprises, in addition, to the above chimeric gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

A series of C-terminus deletion mutants of the B30 endolysin were created in the *E. coli*, T7 polymerase driven expression vector pET21a, in order to identify short protein fragments that retained the lytic activity of the full length protein. Deletion mutant 90 (FIG. 3) lacks the Acm domain, interrupts the CHAP domain, and has no lytic activity against either *S. aureus* or *S. agalactiae*. Deletion mutant 182 contains the full CHAP endopeptidase domain, bisects the Acm glycolase domain between two essential amino acids, is fully active against *S. agalactiae*, but has no activity against *S. aureus*.

Figure 3:
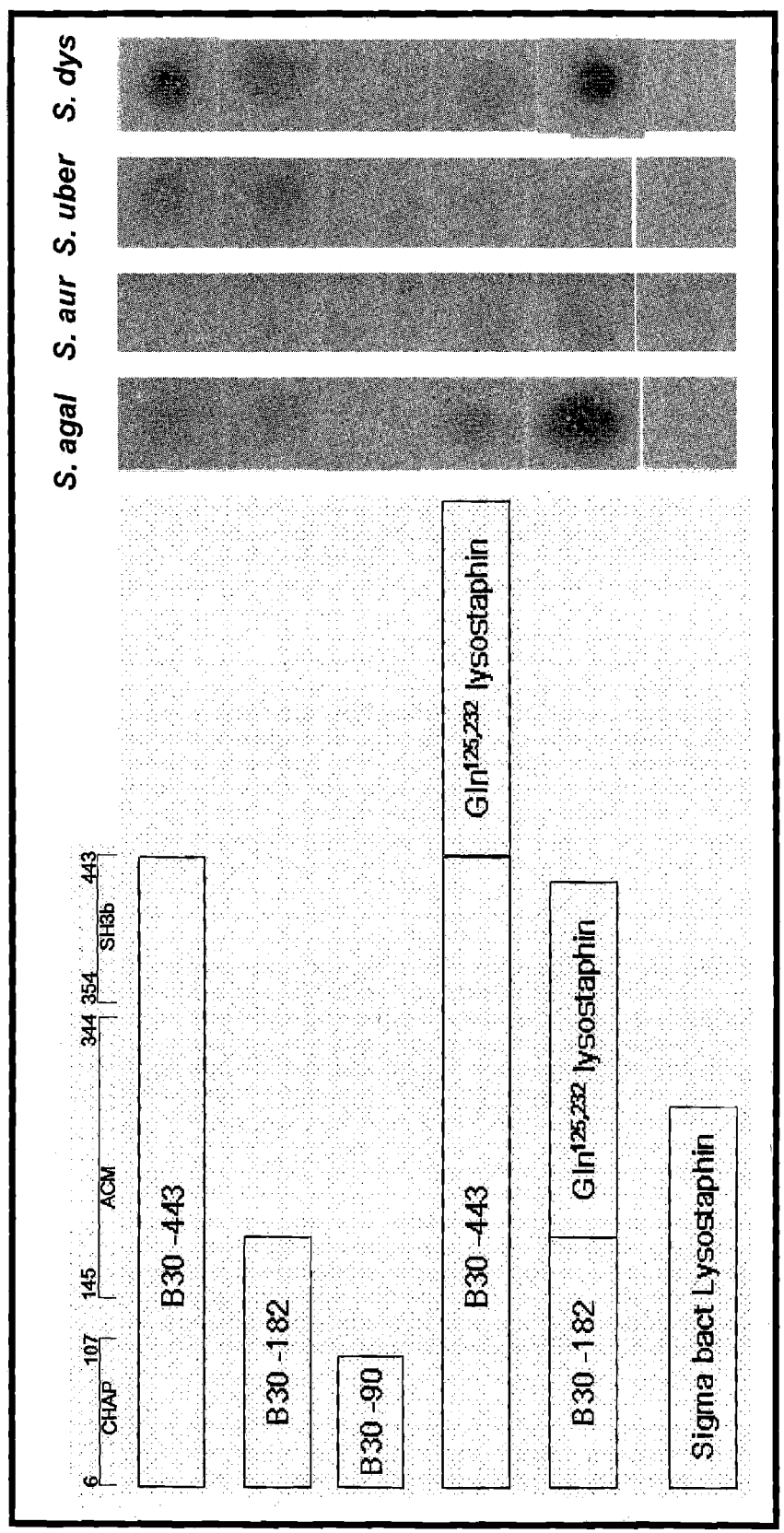
FIG. 3 depicts plate lysis assays of B30 endolysin and lysostaphin constructs. Essential amino acids in both the CHAP endopeptidase and Acm glycolase domains of the B30 endolysin are depicted (Pritchard et al, supra). Crude extracts were prepared for the endolysin constructs (443, 182, 90) and lysostaphin fusion constructs (443-L, 182-L) from *E. coli* harboring the pET21a-derived expression vectors. Cells were grown to mid log phase, amplified with 1 mM IPTG, harvested, washed 3×, and sonicated in lysin buffer A (50 mM Ammonium acetate, 10 mM $CaCl_2$, 1 mM DTT pH 6.2; Pritchard et al, supra), filter sterilized and spotted onto plates containing Tryptic Soy Agar with 0.7% agar, impregnated with heat killed (60° C.×30 sec) bacteria: *S. agalactiae* (*S. agal*), *S. aureus* (*S. aur*), *S. uberis* (*S. uber*), and *S. dysgalactiae* (*S. dys*) and allowed to incubate overnight at room temperature in a humid environment. Spots of cleared lawn represent lysis of the target organism. Identical results were obtained with both live and heat-killed cells. Although similar amounts of extracts were spotted (1-7 µl), none were normalized for the amount of endolysin or lysostaphin activity, thus spot size is not necessarily indicative of activity level. 7 µl of 100 µg/ml of pure Lysostaphin (SIGMA-L; SIGMA Cat. # L0761) in Lysin Buffer A was spotted as a positive control for lysis of *S. aureus*.

Two fusion protein constructs were produced in the same parent expression vector. For the purpose of this application, the full length B30 endolysin open reading frame (ORF) will refer to amino acid #s 1-443 (SEQ ID NO:2) from vector pSD101 (Pritchard et al., supra). The full length ORF was fused to the mature lysostaphin endopeptidase protein coding sequences, lacking the pre-pro signal sequence (amino acid #s 235-480; Heinrich et al. 1987. *Mol. Gen. Genet.* 209 (3): 563-569) to create 443-L. Also, a truncated form of the B30 endolysin gene harboring just the first 182 amino acid (including the entire endopeptidase domain) was fused to the same lysostaphin sequences to create 182-L. *E. coli* extracts harboring either fusion protein show lytic activity towards both pathogens, *S. agalactiae* and *S. aureus*, while extracts from *E. coli* lacking the fusion construct were not lytic for either organism (FIG. 3). As shown in FIG. 3, the fusion proteins also lyse *S. dysgalactiae* and *S. uberis*, i.e., the same streptococcal test species as the parent B30 endolysin.

Figure 4:
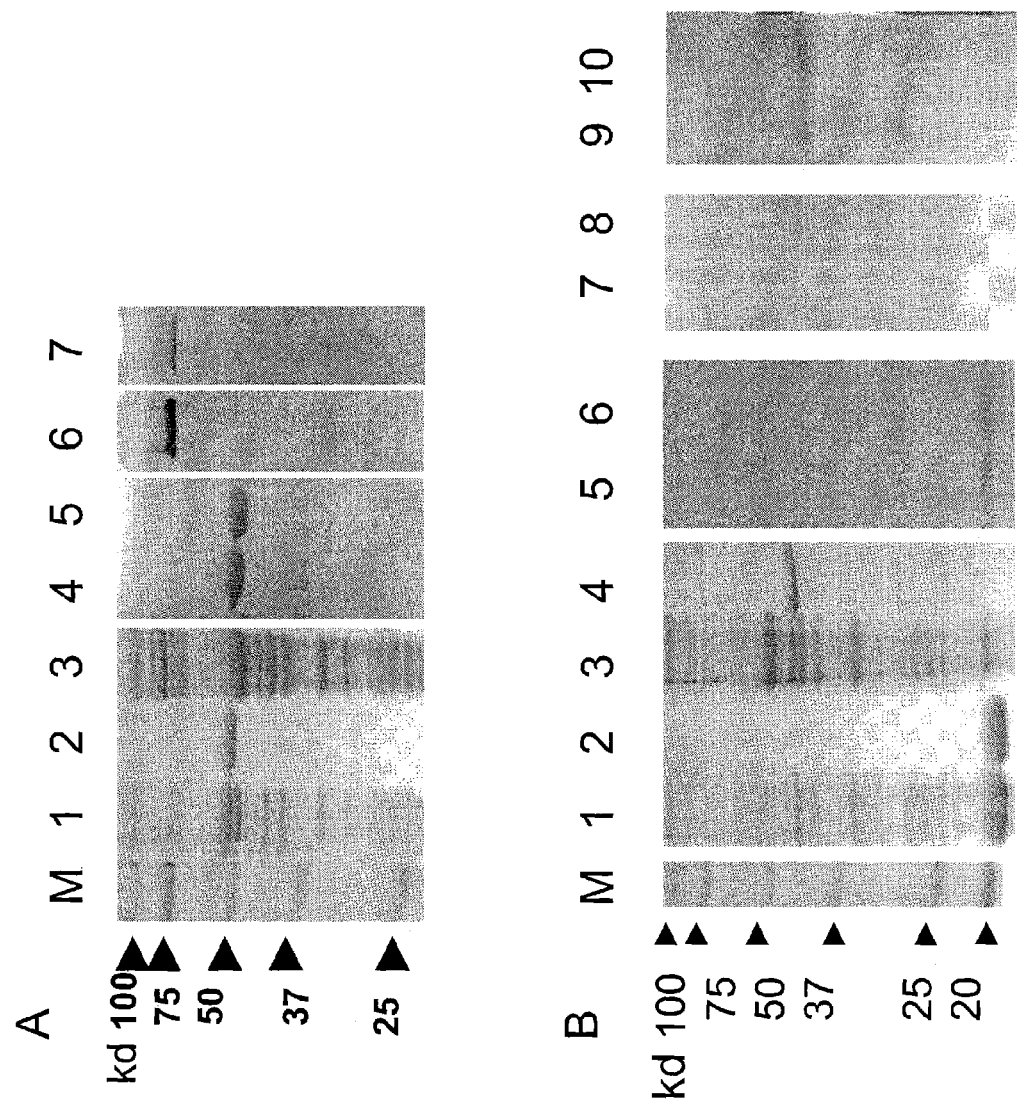
FIGS. 4A and 4B depict the SDS-PAGE and Zymogram analysis of the lysin constructs.

Zymograms were run with either *S. aureus* or *S. agalactiae* cells embedded in the SDS PAGE gel matrix to verify that the fusion proteins were the only proteins in the crude *E. coli* extracts that were responsible for lysis of both *Streptococcus* and *Staphylococcus* (FIG. 4). In all cases, the location of the cleared zones were similar for the crude extracts and the purified proteins, confirming that the lysis activity in the crude extracts was due to the endolysin or fusion protein constructs (FIG. 4). Moreover, the location of the cleared zones in the zymograms is consistent with the predicted size of the truncation and fusion constructs in the crude extract samples (FIG. 4).

The modular nature of the peptidoglycan hydrolase domains is advantageous for creation of the intragenic fusion hydrolase of the invention. The fusion proteins maintain the lytic activity of the parental proteins against both target organisms, demonstrating the efficacy of this approach for designing specific antimicrobials. Additionally, both the deletion mutant 182, and the fusion 182-L maintain their lytic activity against *S. agalactiae*, in the absence of the B30 endolysin carboxyl terminus, demonstrating that the carboxyl terminus of the B30 endolysin is not necessary for substrate recognition in contrast to reports for other endolysins (Lopez et al., supra).

The antimicrobial protein of the invention has been designed to specifically attack both mastitis-causing pathogens, *Staphylococcus aureus* and *Streptococcus agalactiae*. Thus, in treating mastitis, both pathogens could be treated with a single bifunctional fusion endolysin protein.

The mastitis control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products. *E. coli* extracts containing fusion and non-fusion proteins were determined to be effective in a milk-like environment; i.e., extracts were pre-incubated at 37° C. for 30 minutes with or without whey proteins, and then tested in a turbidity reduction assay. All the constructs that gave clearing zones in the plate assays (FIG. 3) also showed a reduction in the turbidity assay (data not shown). Likewise, ingredients may be selected for any given composition which are cooperative in their combined effects whether incorporated for antimicrobial efficacy, physical integrity of the formulation or to facilitate healing and the health of the teat. Generally, the composition comprises a carrier which functions to dilute the active ingredients and facilitates application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

When considering the high level of diversity within bacterial and bacteriophage populations (predicted to be $10^{30}$ bacterial species and $10^{31}$ bacteriophages), and the multiple peptidoglycan hydrolase activities that have already been identified from the few (less than 500) lysins that have been characterized, opportunities for novel antimicrobial design via endolysin activity module shuffling appear limitless. Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmid Constructions

The fusion of lysostaphin to both the truncated (182 amino acid) and full length (443 amino acid) endolysin constructs utilized a lysostaphin construct (BLG-lys; SEQ ID NO:3) which has been reported previously (Kerr et al. 2001. *Nat Biotechnol.* 19(1): 66-70). In BLG-lys, the lysostaphin coding region had been previously truncated to remove the 143 amino acid bacterial signal peptide, and mutated to change two asparagine residues (amino acid #s 125, 232) into glutamine residues (to remove putative eukaryotic oligosaccharide attachment sites). The lysostaphin protein (SEQ ID NO:4) produced is the mature form, 246 amino acids in length. The BGL-lys construct harboring the sequences that encode the mature form was restriction enzyme-digested with NotI and XbaI to isolate a ~4 kb fragment harboring the entire 246 amino acid protein coding region, a ~600 by bovine growth hormone polyA addition region and ~2.5 kb of bovine beta-lactoglobulin 3' proximal gene sequences. The fragment was gel-purified (Qiaquick, QIAGEN), made blunt with T4 polymerase and dNTP's (INVITROGEN), and ligated into the XhoI-site of both pSD101 or the truncated B30-182 construct, which had been blunt-ended and dephosphorylated with Shrimp Alkaline Phosphatase (ROCHE). Fusion of the blunt-ended, Not I cut, lysostaphin gene and blunt ended, Xho I cut, 443 amino acid endolysin gene (or B30-182 gene truncation) generates a gene fusion that in turn generates an in-frame protein fusion at amino acid 443 (or 182), of the phage endolysin sequences to amino acid 1 of the mature lysostaphin sequences, with the addition of no introduced amino acid codons at the fusion site.

Example 2

Growth of Bacteria, Extract Preparation, Protein Purification and Analysis

All assays were performed on extracts of *E. coli* BL21 (DE3) (NOVAGEN) cells harboring the constructs described above. Cell extracts were prepared by growth of bacteria in 100 ml Superbroth, 100 µg/ml Ampicillin at 37° C. with shaking. At midlog phase ($A_{660}$ of 0.3-0.5), induction of the T7-lacZ hybrid promoter was achieved with a final concentration of 1 mM IPTG followed by incubation at 37° C. with shaking for 3-4 hours. Cells were then pelleted and washed 3× with Lysin Buffer A (50 mM Ammonium Acetate, 10 mM $CaCl_2$, 1 mM DTT pH 6.2), and pellets frozen at −80° C. Pellets could be thawed and resuspended (up to 20 days later) in 1 ml Lysin Buffer A, disrupted with 6×5 second pulses of sonication on ice with 5 second rest periods between pulses. Lysates were cleared with a 10 minute spin in a microfuge at 4° C., filter-sterilized through a Millex 0.22 micron pore sterile filter and stored at −80° C. for up to 5 months with no apparent loss of activity.

Fusion proteins were purified from *E. coli* cell extracts by nickel affinity chromatography (QIAGEN Ni-NTA Agarose. Datasheet [online]. QIAGEN, Inc. 2003-2005. [retrieved on 2005-00-00]. Retrieved from the Internet: <URL: www1.qiagen.com/products/protein/purification/qiaexpressproteinpurificationsystem/ntaagarose.aspx>). Either mini-spin columns or five-ml nickel columns containing superflow Ni-NTA or Ni-NTA agarose resin were utilized. The effluent was desalted with BioSpin B30 columns (BIO-RAD) to remove phosphate ions, before use, e.g., in turbidity assays.

Zymograms were run with either *S. aureus* or *S. agalactiae* cells embedded in the SDS PAGE gel matrix to verify that the fusion proteins were the only proteins in the crude *E. coli* extracts that were responsible for lysis of both *Streptococcus* and *Staphylococcus* (FIG. 4). The zymograms were run in parallel with an identical 15% SDS-PAGE and the same gel mix was used for both. Cells were added to the gel mix in lysin buffer A. These target cells were obtained from 100 ml of mid-log phase culture, washed 1× with lysin buffer A, and resuspended in 1 ml of lysin buffer A. Four hundred microliters of cells in lysin buffer A and 4 µl 10% SDS were added to the Zymogram Gel Mix prior to addition of ammonium persulfate and TEMED. 400 µl of lysin buffer A was substituted for the cell suspension in the control PAGE. Gels were run at 131 volts for 1.5 hours in the BIORAD Mini-PROTEAN 3 gel apparatus. Zymograms were soaked 1 hour in distilled water to remove SDS and then incubated at room temperature in lysin buffer A overnight. Control SDS gels were put directly into BIORAD BioSafe Coomassie stain (BIORAD) for one hour and then rinsed in distilled water overnight.

In all cases, the location of the cleared zones were similar for the crude extracts and the purified proteins, confirming that the lysis activity in the crude extracts was due to the endolysin or fusion protein constructs (FIG. 4). Moreover, the location of the cleared zones in the zymograms is consistent with the predicted size of the truncation and fusion constructs in the crude extract samples (FIG. 4).

Example 3

Generation of Deletion Mutant pDMD90

The 443 codon B30 endolysin gene was subcloned between the unique NdeI and XhoI sites of the parent pET21a (NOVAGEN) vector by Pritchard et al. (supra) which added two codons at the carboxyl terminus. pET21a has a lacZ-T7 promoter fusion for high level expression induction with IPTG and a series of six in-frame Histidine codons which add a His Tag at the C-terminus of the resultant endolysin protein. The B30 endolysin gene fragment encoding the first 90 amino acids was subcloned back into the parent vector pSD101 (after removal of the full length endolysin gene). The 90 codon harboring DNA fragment was amplified using two oligonucleotides as PCR primers, each with the following sequences: forward primer BGLF: 5'-TCC GGC GTA GAG GAT CGA GAT 3' (SEQ ID NO:5) and reverse primer 90R: 5'-TGC TAC ATG CTC GAG AGG CGT 3' (SEQ ID NO:6). The forward primer overlaps the BglII site located immediately 5' to the T7 promoter region in the pSD101 expression vector. The reverse primer contains a region of degeneracy that generated an XhoI restriction enzyme site in the PCR-amplified fragment at amino acid codon 90 of the B30 endolysin gene. The resultant BglII-XhoI-digested and agarose gel-purified PCR-generated fragment was ligated and subcloned into the parent vector pSD101 which had been similarly digested, phosphatased (Shrimp Alkaline Phosphatase; ROCHE) and agarose gel-purified, using conventional methods and reagents. Ligations were transformed into *E. coli* DH5alpha (INVITROGEN). The final construct removes the amino acids 91 thru 443 (inclusive) and religates amino acid 90 to amino acid 444, in frame, thus maintaining the His tag.

Example 4

Generation of Deletion Mutant pDMD182

In order to create pDMD182, the construct harboring the first 182 amino acids of the B30 endolysin, a two step process was used to introduce the 182-lysostaphin (182-Lyso) fusion into the eukaryotic expression vector pcDNA3.1 (INVITROGEN). First, the 182-Lyso coding region was introduced into pET21a to reconstitute the His6 tag on the C-terminal end of the fusion. Amplifications of the 182-Lyso coding sequences were performed with the forward primer BGLF (described above) and a reverse primer [LYSOR: 5'-GCC CTC AGT CGA CAC TAG TCC ACA GAA CAC-3' (SEQ ID NO:7)] with a unique SalI site inserted immediately before the translational stop signal of the lysostaphin open reading frame. The PCR product was gel purified, digested with BglII and SalI, and desalted as described above. This BglII-SalI ended fragment was ligated into pET21a that was double digested with BglII and XhoI, and dephosphorylated as described above. Ligations, and transformations were as described above, with the final construct verified with restriction enzyme mapping and peptidoglycan hydrolase activity measurements. Constructs containing T7-lacZ promoters were first transformed into *E. coli* DH5α (INVITROGEN), and positive clones (by restriction enzyme mapping) were then introduced into *E. coli* BL21(DE3) (NOVAGEN) cells. After induction and sonication of the cells, extracts were tested for enzyme activity. In the second step, the 182-Lyso His-tagged construct was moved into pcDNA3.1. Amplification was performed using a forward primer [KOZF: 5'-TTC GAT ATC GCG GCC GCA ACC ATG GCA ACT TAT CAA-3' (SEQ ID NO:8)] harboring an EcoRV site immediately 5' to a consensus eukaryotic translational start site (Kozak, M. 1984. *Nucleic Acids Res.* 12: 857-872) and a reverse primer [182HR: TCG GAA TIC GTT AGC AGC CGG AAT C-3' (SEQ ID NO:9)] harboring an EcoRI site, following the His6 tag and translational stop signal. The amplification product was digested with EcoRI and EcoRV and subcloned into similarly cut and dephosphorylated pcDNA3.1 as described above.

Example 5

Plate Assays

Results were identical on plate assays performed on either live or heat killed bacteria. *Streptococcus (agalactiae, dysgalactiae,* and *uberis*) or *Staphylococcus aureus* were grown in BHI media at 37° C. with shaking to mid log phase ($A_{660}$=0.3-0.5), pelleted and resuspended at approximately 10× original concentration in either media (live) or Lysin Buffer A (heat killed), and stored at 4° C. or heat killed immediately with incubation at 60° C.×30 minutes and then stored up to 1 month at 4° C. Both live and heat killed cells were diluted ~7× (final dilution empirically determined) in 50° C., 0.7% Bacto Tryptic Soy Agar (Becton Dickinson) and immediately poured into sterile petri dishes, and allowed to solidify at room temp. Sterile extracts prepared above (5 µl) were spotted onto the solidified agar plates and monitored for clearing at intervals up to 24 hours. No quantification of extract lytic activity was performed. 5 µl of 100 µg/ml (in Lysin Buffer A) of recombinant Lysostaphin (SIGMA, # L0761) was spotted as a positive control for lysis of *S. aureus*.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

I claim:

1. An isolated recombinant bifunctional endolysin fusion protein, wherein said fusion protein comprises an endolysin comprising contiguous amino acid residues 1-443 of SEQ ID NO:2 from Group B *Streptococcus* B30 bacteriophage, wherein the endolysin comprises at least a D-alanyl-L-alanine endopeptidase amino terminus (CHAP) domain, and an Acm glycolase (lysozyme-like) domain, further comprising four mutations C26S, H91A, D158A and E185A, wherein the C-terminal end of the endolysin is fused in-frame to the N-terminal end of the lysostaphin comprising contiguous amino acid residues 1-246 of SEQ ID NO:4, wherein the lysostaphin further comprises two mutations at residues 125 and 232 to glutamine, wherein the fusion protein has antimicrobial activity and kills *Staphylococcus aureus* bacteria and *Streptococcus agalactiae, S. dysgalactia*, and *S. uberis* bacteria.

2. An isolated recombinant bifunctional fusion protein, wherein the fusion protein comprises an endolysin comprising contiguous amino acid residues 1-182 of SEQ ID NO:2 from Group B *Streptococcus* B30 bacteriophage, wherein the endolysin comprises at least a D-alanyl-L-alanine endopeptidase amino terminus (CHAP) domain, and an Acm glycolase (lysozyme-like) domain, further comprising three mutations C26S, H91A and D158A, wherein the C-terminal end of the endolysin is fused in-frame to the N-terminal end of the lysostaphin comprising contiguous amino acid residues 1-246 of SEQ ID NO:4, wherein the lysostaphin further comprises two mutations at residues 125 and 232 to glutamine, wherein the fusion protein has antimicrobial activity and kills *Staphylococcus aureus* bacteria and *Streptococcus agalactiae, S. dysgalactia*, and *S. uberis* bacteria.

3. A composition for the treatment of a disease caused by more than one genus or species of bacteria, wherein said composition contains the isolated recombinant bifunctional fusion protein of claim 1 or claim 2 and a pharmaceutically acceptable carrier.

4. A method of treating a disease caused by more than one genus or species of bacteria by administering the isolated recombinant bifunctional fusion protein of claim 1.

5. A method of treating a disease caused by more than one genus or species of bacteria by administering the isolated recombinant bifunctional fusion protein of claim 2.

6. The method of treating a disease caused by more than one genus or species of bacteria by administering the isolated recombinant bifunctional fusion protein of claim 1 or claim 2, wherein said disease is mastitis.

* * * * *